(12) United States Patent
Pawar et al.

(10) Patent No.: US 8,415,019 B2
(45) Date of Patent: Apr. 9, 2013

(54) CERAMIC LAYERED MEDICAL IMPLANT

(75) Inventors: Vivek Devidas Pawar, Germantown, TN (US); Shilesh C. Jani, Memphis, TN (US); Carolyn L. Weaver, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 12/663,500

(22) PCT Filed: Jun. 11, 2008

(86) PCT No.: PCT/US2008/066589
§ 371 (c)(1),
(2), (4) Date: Dec. 7, 2009

(87) PCT Pub. No.: WO2008/154593
PCT Pub. Date: Dec. 18, 2008

(65) Prior Publication Data
US 2010/0174383 A1  Jul. 8, 2010

Related U.S. Application Data

(60) Provisional application No. 60/943,180, filed on Jun. 11, 2007.

(51) Int. Cl.
*B32B 15/04* (2006.01)
*A61F 2/02* (2006.01)

(52) U.S. Cl. ........ 428/469; 428/688; 428/689; 428/697; 428/698; 428/699; 428/701; 428/702; 428/704; 623/23.53; 623/23.56

(58) Field of Classification Search .......... 428/469, 428/688, 689, 697, 698, 699, 701, 702, 704; 623/23.53, 23.56
See application file for complete search history.

(56) References Cited

U.S. PATENT DOCUMENTS

| 2,987,352 | A  | * | 6/1961 | Watson ......... 384/297 |
| 5,037,438 | A  | * | 8/1991 | Davidson ...... 623/22.15 |
| 5,152,794 | A  | * | 10/1992 | Davidson ...... 623/23.6 |
| 5,372,660 | A  | * | 12/1994 | Davidson et al. ...... 148/421 |
| 5,415,704 | A  | * | 5/1995 | Davidson ...... 148/316 |
| 6,395,327 | B1 | * | 5/2002 | Shetty ......... 427/2.26 |
| 6,447,550 | B1 | * | 9/2002 | Hunter et al. ...... 623/22.15 |
| 6,585,772 | B2 | * | 7/2003 | Hunter et al. ...... 623/23.54 |
| 6,793,681 | B1 | * | 9/2004 | Pope et al. ...... 623/22.15 |
| 6,833,197 | B1 | * | 12/2004 | Morton et al. ...... 428/472.1 |
| 6,869,701 | B1 | * | 3/2005 | Aita et al. ...... 428/698 |
| 7,105,030 | B2 | * | 9/2006 | Despres et al. ...... 623/23.36 |
| 7,393,589 | B2 | * | 7/2008 | Aharonov et al. ...... 428/469 |
| 7,473,278 | B2 | * | 1/2009 | Hunter et al. ...... 623/23.39 |

(Continued)

OTHER PUBLICATIONS

Examiner's report of Chinese Application 200880102902.0, Titled "Ceramic Layered Medical Implant," issued on Sep. 6, 2012, 8 pages, with English translation.

*Primary Examiner* — Jennifer McNeil
*Assistant Examiner* — Lauren Colgan
(74) *Attorney, Agent, or Firm* — David A. Chambers; David A. Warmbold

(57) ABSTRACT

A new composition and medical implant made there from comprises a thick diffusion hardened zone, and layered ceramic surface. Orthopedic implants comprising the new composition, methods of making the new composition, and methods of making orthopedic implants comprising the new composition are disclosed.

18 Claims, 11 Drawing Sheets

U.S. PATENT DOCUMENTS

| | | | |
|---|---|---|---|
| 7,541,102 B2* | 6/2009 | Klippe et al. | 428/701 |
| 7,550,209 B2* | 6/2009 | Pawar et al. | 428/701 |
| 7,578,851 B2* | 8/2009 | Dong et al. | 623/22.21 |
| 7,896,926 B2* | 3/2011 | Hunter et al. | 623/23.56 |
| 7,931,683 B2* | 4/2011 | Weber et al. | 623/1.42 |
| 7,968,209 B2* | 6/2011 | Pawar et al. | 428/632 |
| 8,172,958 B2* | 5/2012 | Pawar et al. | 148/217 |
| 2003/0220699 A1* | 11/2003 | Hunter et al. | 623/23.54 |
| 2004/0002766 A1* | 1/2004 | Hunter et al. | 623/20.21 |
| 2004/0122524 A1* | 6/2004 | Hunter et al. | 623/22.18 |
| 2005/0033442 A1* | 2/2005 | Fisher et al. | 623/18.11 |
| 2005/0084705 A1* | 4/2005 | Klippe et al. | 428/633 |
| 2006/0058888 A1* | 3/2006 | Hunter et al. | 623/23.39 |
| 2006/0259150 A1* | 11/2006 | Hunter et al. | 623/22.15 |
| 2007/0137734 A1* | 6/2007 | Pawar et al. | 148/206 |
| 2008/0281429 A1* | 11/2008 | Pawar et al. | 623/23.6 |
| 2008/0289729 A1* | 11/2008 | Pawar et al. | 148/559 |
| 2009/0012611 A1* | 1/2009 | Brosnahan et al. | 623/11.11 |
| 2009/0074836 A1* | 3/2009 | Pawar et al. | 424/423 |
| 2009/0112331 A1* | 4/2009 | Hunter et al. | 623/23.53 |
| 2010/0174383 A1* | 7/2010 | Pawar et al. | 623/23.56 |
| 2011/0139312 A1* | 6/2011 | Hunter et al. | 148/403 |
| 2011/0320007 A1* | 12/2011 | Pawar et al. | 623/23.53 |

* cited by examiner

US 8,415,019 B2

CERAMIC LAYERED MEDICAL IMPLANT

CROSS-REFERENCE TO RELATED APPLICATIONS

This application is a National Phase of International Application No. PCT/US2008/066589, filed Jun. 11, 2008 which claims priority to U.S. Provisional Application Ser. No. 60/943,180, filed on Jun. 11, 2007. Each prior application is incorporated by reference herein in its entirety.

TECHNICAL FIELD

The present invention relates to a ceramic layered metallic medical implant manufactured from zirconium or a zirconium alloy. The new composition has application, for example, in articulating and non-articulating surfaces of medical implants. The present invention also relates to orthopedic implants comprising the new composition, methods of making the new composition, and methods of making medical implants comprising the new composition. While the present implant composition is useful in hard-on-soft applications (e.g., a medical implant component of the present invention articulating against polyethylene), the present invention also encompasses the use of this new medical implant composition in hard-on-hard applications (e.g., the present composition articulating against itself or against other hard materials and ceramics) in a hip, knee, spine, or other implant.

BACKGROUND OF THE INVENTION

Medical implant materials, in particular orthopedic implant materials, seek to combine high strength, corrosion resistance and tissue compatibility. The longevity of the implant is of prime importance especially if the recipient of the implant is relatively young because it is desirable that the implant function for the complete lifetime of a patient. Because certain metal alloys have the required mechanical strength and biocompatibility, they are ideal candidates for the fabrication of prostheses. These alloys include 316L stainless steel, chrome-cobalt-molybdenum alloys (CoCr), titanium alloys and more recently zirconium alloys which have proven to be the most suitable materials for the fabrication of load-bearing and non-load bearing prostheses.

To this end, oxidized zirconium orthopedic implants have been shown to significantly reduce polyethylene wear of the oxidized zirconium orthopedic implants articulating against a polyethylene surface. The use of oxide surfaces such as oxidized zirconium in orthopedic applications was first demonstrated by Davidson in U.S. Pat. No. 5,037,438. Previous attempts have been made to produce oxidized zirconium layers on zirconium alloy parts for the purpose of increasing their abrasion resistance. One such process is disclosed in U.S. Pat. No. 3,615,885 to Watson which discloses a procedure for developing thick (up to 0.23 mm) oxide layers on Zircaloy 2 and Zircaloy 4. However, this procedure results in significant dimensional changes, and the oxide film produced does not exhibit especially high abrasion resistance.

U.S. Pat. No. 2,987,352 to Watson discloses a method of producing a blue-black oxide layer on zirconium alloy parts for the purpose of increasing their abrasion resistance. The blue-black color is the appearance of the zirconium oxide formed on the surface. Both U.S. Pat. No. 2,987,352 and U.S. Pat. No. 3,615,885 produce a zirconium oxide layer on zirconium alloy by means of air oxidation. U.S. Pat. No. 3,615,885 continues the air oxidation long enough to produce a beige layer of greater thickness than the blue-black layer of U.S. Pat. No. 2,987,352. The beige appearance was sighted to be due to the fine micro-cracks on the surface of the oxide. The presence of micro-cracks may lead to spalling or removal of surface oxide particulates thus may not be applicable to many components where there are two work faces in the close proximity.

The blue-black layers have a thickness which is less than that of the beige layer although the hardness of the blue-black layer is similar to that of the beige layer. This blue-black oxide layer lends itself better to surfaces such as prosthetic devices. Although the blue-black layer is more abrasion resistant than the beige layer it is a relatively thin layer.

As discussed above, U.S. Pat. No. 5,037,438 to Davidson discloses a method of producing zirconium alloy prostheses with a oxidized zirconium surface. U.S. Pat. No. 5,180,394 to Davidson discloses orthopedic implants with blue-black zirconium oxide or zirconium nitride surfaces. U.S. Pat. No. 2,987,352 to Watson discloses a method of producing zirconium bearings with an oxidized zirconium surface. The oxide layer produced is not always uniform in thickness and the non-uniformity reduces the integrity of the bonding between the zirconium alloy and the oxide layer and the integrity of the bonding within the oxide layer. Both U.S. Pat. No. 2,987,352 and U.S. Pat. No. 5,037,438 are incorporated by reference as though fully set forth herein.

In U.S. Pat. Nos. 6,447,550 and 6,585,772 and U.S. Patent Publication No. 2006/0058888, Hunter, et al. describes methods for obtaining an oxidized zirconium layer of uniform thickness. Hunter teaches that such is obtained by applying pre-oxidation treatment techniques and by manipulation of substrate microstructure. The use of uniform thickness oxide layer results in increased resistance to corrosion by the action of the body fluids as well as other benefits and is biocompatible and stable over the lifetime of the recipient. U.S. Pat. Nos. 6,447,550 and 6,585,772 and U.S. Patent Publication No. 2006/0058888 are incorporated by reference as though fully set forth herein.

Zirconium alloys are typically soft. The hardness of such alloys can range from 1.5 to 3 GPa. Since these alloys are soft, they can be easily abraded with a harder material. As described in the prior art, the abrasion resistance of zirconium alloys can be improved by oxidizing or nitriding these alloys. The significant reduction in wear of polyethylene against oxidized zirconium surfaces is attributed to the harder ceramic nature of the oxide. The hardness of the zirconium oxide surface is approximately 12 GPa. The oxidized zirconium implant typically has a 5 to 6 micron thick ceramic surface (zirconium oxide) that is formed by a thermally driven diffusion process in air. Below the zirconium oxide is a hard, oxygen-rich diffusion layer of approximately 1.5 to 2 microns. Below the diffusion zone is the softer zirconium alloy matrix. FIG. 1 shows a schematic cross-sectional view of such and oxidized zirconium structure taught by Davidson and Hunter (herein referred to "Davidson-type" oxidized zirconium) and FIG. 2 shows the hardness profile of the Davidson-type oxidized zirconium (M. Long, L. Reister and G. Hunter, Proc. $24^{th}$ Annual Meeting of the Society For Biomaterials, Apr. 22-26, 1998, San Diego, Calif., USA).

Oxidized zirconium has been a great advancement over the conventional cobalt chromium and stainless steel alloys. There is still room for improvement. The totality of hardened zones (oxide plus diffusion hardened alloy) render the implant resistant to microscopic abrasion (for example, from third bodies such as bone cement, bone chips, metal debris, etc.) and slightly less resistant to macroscopic impact (surgical instrumentation and from dislocation/subluxation contact with metallic acetabular shells). The smaller hardening depth of these implants renders them less than optimal for hard-on-hard applications although such use has been suggested by Hunter and Mishra (U.S. Pat. No. 6,726,725). Hunter '725 teaches that the oxide thickness can be increased up to 20 microns for such applications. But Davidson-type oxide compositions having such thicknesses, although highly wear-resistant, can have significant number of oxide layer defects when the oxide thickness is increased to 20 microns. Such defects can lead to localized spalling of the oxide. Also, in the Davidson-type composition below the oxide, there is a relatively small diffusion hardened zone. Thus, while the Davidson-type compositions exhibited superior wear resistance compared to many conventional materials, there is room for improvement.

In a hard-on-hard application such as in a hip joint, the material articulates against itself or another hardened or non-hardened metal instead of polyethylene. The wear rates in such types of implants could be as high as 1 micron per year. With the totality of the hardened zone (oxide and diffusion zone) having a thickness of less than 7 microns (approximately 5 micron oxide and 2 micron diffusion hardened zone below the oxide), Davidson-type oxidized zirconium implants, although representing the state-of-the-art when originally introduced and still quite useful, have room for improvement in such applications.

Currently, there are two primary types of hard-on-hard hip implants that are available commercially, namely metal-on-metal and ceramic-on-ceramic. The current standard material of metal-on-metal implants is high carbon Co—Cr alloy. The major concern with the metal-on-metal implant is the metal ion release from the joint and its unknown effects on the physiology of the human body. The advantage of metal-on-metal implants is that they can be used in larger sizes. The larger size of the implant allows greater range of motion and stability of the implant. The metal-on-metal implants have also been shown to be useful for resurfacing type of application where conservation of bone is desired. In such larger joints, the conventional or cross-linked polyethylene is not preferred and metal-on-metal may be the only choice available. The larger size requires polyethylene liner to be thinner. A thinner liner may not be mechanically strong, may creep more or may lead to increased wear and osteolysis and eventually failure of the implant. The other commonly used hard-on-hard implant material is ceramic-on-ceramic. The current standard material of ceramic-on-ceramic implants is alumina. The surface hardness of the alumina is approximately 20 to 30 GPa. Metal ion release is typically not a concern for these implants. But due to limited toughness and the brittle nature of ceramics, it is difficult to make these implants in larger sizes. The ceramic components have finite probability of fracture thus leading to a potential joint failure and complications associated with the fracture of a joint.

One of the ways to improve the surface hardness of oxidized zirconium is to form a zirconium nitride instead of zirconium oxide. Kemp (U.S. Pat. No. 5,399,207) describes a method to make oxidized or nitrided zirconium compositions using a fluidized bed furnace. Kemp states that the nitridation can be carried out from 1300° F. (700° C.) to 1600° F. (870° C.). Kemp teaches use of pure nitrogen instead of air or oxygen to achieve the nitridation of the surfaces. U.S. Pat. No. 5,180,394 to Davidson discloses orthopedic implants with blue-black zirconium oxide or zirconium nitride surfaces. Note that zirconium nitride typically appears yellowish-golden and thus can be distinguished from blue-black zirconium oxide. Davidson teaches that the nitride layer to be formed at 800° C. in about one hour in nitrogen atmosphere. Use of such high temperature can lead to micro-structural changes such as grain growth. These changes in-turn may affect the mechanical properties of the substrate. Higher temperature process can also dimensionally distort the components being manufactured. It should be noted that the zirconium nitride may not adhere as well as zirconium oxide does to the zirconium alloy substrate. It should also be noted that in all the prior art, the methods employed make zirconium oxide or make zirconium nitride.

The art of increasing depth of hardening in titanium alloys has been described previously. It involves, basically one of forming an oxide on the surface of the article by treatment in an oxygen-rich environment, followed by heat treating the article in an oxygen-deficient inert environment. One of the approaches provided by Takamura (Trans JIM, vol. 3, 1962, p. 10) has been to oxidize a titanium sample followed by treating it in an inert gas such as argon gas. This apparently allows oxygen to diffuse in the substrate and form a thick diffusion zone. Presence of oxygen in the diffusion zone leads to hardening. Another approach suggested by Dong et al. (U.S. Pat. No. 6,833,197) is to use vacuum or an inert gas to achieve an oxygen-deficient environment, thereby achieving the diffusion-hardening after oxidation. The preferred temperature specified by both Takamura and Dong et al for oxidation is 850° C. and that for diffusion hardening (vacuum treatment) is 850° C. Use of such high temperature can lead to micro-structural changes such as grain growth. These changes in-turn may affect the mechanical properties of the substrate. Higher temperature process can also dimensionally distort the components being manufactured. Dong et al suggest this methodology for titanium and zirconium and titanium/zirconium alloys. One of the problems with these methods, particularly for zirconium alloys, is that the oxidation and diffusion hardening temperatures are significantly high and can lead to thick and cracked (defective) oxide as well as cracks in the substrates after diffusion hardening. Dong demonstrates its method using titanium alloys; no examples for zirconium/niobium-based or titanium/zirconium/niobium-based alloys have been shown. Further, both Dong and Takamura require complete dissolution of the oxide in the substrate in an inert atmosphere such as argon or in vacuum. Dong also teaches a sigmoid shaped hardness profile of the diffusion hardened metallic zone as a result of this complete dissolution of the oxide. The sigmoid shaped diffusion hardened zone profile requires complete dissolution of the oxide in the substrate. Another approach is suggested by Pawar et al. (U.S. Patent Application No. 20070137734). Pawar et al. teach a method to obtain depth of hardening and a defect-free ceramic surface by carefully controlling the temperature and time of oxidation and of the vacuum diffusion treatment. Pawar et al. also teach the method to form an error-function type layered hardness profile of the diffusion hardened zone. However, the method teaches formation of only one type of defect-free ceramic layer such as oxide or nitride. U.S. Pat. No. 6,833,197 and U.S. Patent Publication No. 20070137734 are incorporated by reference as though fully set forth herein.

Previously shown methods either increase the surface hardness at the expense of lowering the adherence of the surface layer to the substrate and limiting the depth of hardening, or, conversely, increase the depth of hardening by heat treating in an inert gas atmosphere at the expense of creating surface deformations and adversely affecting surface hardness. In some methods defect-free ceramic layer is obtained with increased depth of hardening. In all these methods, the surface has only one ceramic layer. The inventors of the present invention have discovered that instead of using vacuum or inter atmosphere, a reactive gas can be employed.

This reactive gas in-turn will transform the surface layer to the different type of ceramics such as nitrides or oxides or oxynitrides. This produces a layered ceramic structure of a composition which has not been shown in the prior art. This layered ceramic structure thus can be tailored to take advantage of the ceramic surface formed. For example, the first layer on the surface could be hard zirconium nitride which is a highly reflective golden appearance surface. The layer underneath this nitride could be blue-black zirconium oxide. Several such combinations of layers can be made to achieve the surface hardness and the specific characteristics of those ceramic layers.

BRIEF SUMMARY OF THE INVENTION

In one embodiment of the present invention, there is a medical implant comprising: a substrate comprising zirconium or zirconium alloy; a diffusion hardened zone in contact with said substrate, said diffusion hardened zone comprising zirconium or zirconium alloy and a diffusion hardening species, said diffusion hardened zone having a thickness of greater than 2 microns; and, optionally, a ceramic zone having a layered structure comprising at least two layers wherein said ceramic zone is in contact with said diffusion hardened zone, and said ceramic layers range in thickness from 0.1 to 25 microns; and wherein the total thickness of the ceramic zone and the diffusion hardened zone is 5 microns or greater.

In some embodiments, the ceramic zone is present and comprises a layered structure comprising at least two layers wherein said ceramic zone is in contact with said diffusion hardened zone, and said ceramic layers range in thickness from 0.1 to 25 microns.

In some embodiments, a layer in the ceramic zone comprises zirconium, oxygen, nitrogen, boron, carbon or any combination thereof.

In some embodiments, the substrate further comprises titanium, tantalum, hafnium, niobium, or any combination thereof.

In some embodiments, the layered ceramic zone comprises three layers and having: a surface layer comprising zirconium, and nitrogen, a second layer adjacent to the surface layer comprising zirconium, oxygen and nitrogen; and, a third layer adjacent to the said second layer comprising zirconium and oxygen.

In some embodiments, the layered ceramic zone comprises two layers and having: a surface layer comprising zirconium, oxygen and nitrogen; and, a second layer adjacent to the said surface layer comprising zirconium and oxygen.

In some embodiments, the layered ceramic zone comprises two layers and having: a top layer comprising zirconium and nitrogen, and a second layer adjacent to the said top layer comprising zirconium and oxygen.

In some embodiments, individual layers of the layered ceramic zone have a thickness of 0.1 micron to 10 microns.

In some embodiments, the total thickness of the layered ceramic zone is 0.5 micron to 50 microns In some embodiments, the ceramic zone forms a surface of said implant and said layered diffusion zone lies below said ceramic zone.

In some embodiments, the diffusion hardened zone has a layered structure comprising at least two distinct layers under metallographic analysis.

In some embodiments, the diffusion hardened zone comprises a diffusion hardening species selected from the group consisting of oxygen, nitrogen, boron, carbon, and any combination thereof.

In some embodiments, the diffusion hardening species comprises oxygen, and/or nitrogen.

In some embodiments, the diffusion hardened zone has a concentration of oxygen which decreases in the direction of the substrate, said decrease of oxygen concentration being defined by a function of selected from the group consisting of an error function, an exponential function, near uniform distribution function, and any sequential combination thereof.

In some embodiments, the first layer of said diffusion hardened zone has a thickness which is greater than or equal to the thickness of said second layer and of any additional layers if any said additional layers are present.

In some embodiments, the diffusion hardened zone has a thickness of 5 to 70 microns.

In some embodiments, the diffusion hardened zone has a thickness of 10 to 50 microns.

In some embodiments, the diffusion hardened zone has a thickness of 2 microns to 100 microns.

In some embodiments, the hardness of the diffusion hardened zone is at least 10% greater than that of the substrate.

In some embodiments, the substrate comprises an alloy of zirconium and niobium and has a niobium content of at least 1% (w/w).

In some embodiments, the substrate comprises an alloy of zirconium and niobium and has a niobium content of at least 10% (w/w).

In some embodiments, the medical implant is selected from the group consisting of a shoulder implant, elbow orthopedic implant, vertebral implant, a hip implant, a knee implant, and a spinal implant.

In some embodiments, there is a method of making a layered ceramic medical implant comprising the steps of: forming said medical implant of zirconium or zirconium alloy; treating said implant in the presence of ceramic-forming species at temperature of 500 to 1000° C. for greater than 2 minutes; and, thereafter treating said implant under a reactive gas at a temperature of 500 to 1000° C.

In some embodiments, the steps of forming said medical implant of zirconium or zirconium alloy, treating said implant in the presence of ceramic-forming species at temperature of 500 to 1000° C. for greater than 2 minutes, and thereafter treating said implant under a reactive gas at a temperature of 500 to 1000° C. are repeated.

In some embodiments, the step of treating said implant in the presence of ceramic-forming species at temperature of 500 to 1000° C. for greater than 2 minutes is performed for between 5 minutes and 12 hours.

In some embodiments, the step of thereafter treating said implant under a reactive gas at a temperature of 500 to 1000° C. is performed for between 15 minutes to 30 hours.

In some embodiments, the step of thereafter treating said implant under a reactive gas is carried out in nitrogen.

In some embodiments, the step of thereafter treating said implant under a reactive gas is carried out in methane.

In some embodiments, the step of treating is carried out by placing the implant in a solid reactive mixture.

In some embodiments, the step of treating said implant in the presence of ceramic-forming species at temperature of 500 to 1000° C. for greater than 2 minutes is carried out in a nitrogen atmosphere.

In some embodiments, the step of treating said implant in the presence of ceramic-forming species at temperature of 500 to 1000° C. for greater than 2 minutes is carried out in a nitrogen and argon mixture.

In some embodiments, the step of treating said implant in the presence of ceramic-forming species at temperature of 500 to 1000° C. for greater than 2 minutes is carried out in a methane and nitrogen mixture.

In some embodiments, said reactive gas is are present at a partial pressure of from less than $10^{-4}$ to 760 Torr.

In some embodiments, the said reactive gas is are present at a partial pressure of 0.05 to 500 Torr.

In some embodiments, the step of treating said implant in the presence of ceramic-forming species at temperature of 500 to 1000° C. for greater than 2 minutes and said step of thereafter treating said implant under a reactive gas at a temperature of 500 to 1000° C. comprise treating said implant with a diffusion hardening species selected from the group consisting of oxygen, nitrogen, boron, carbon, and any combination thereof.

In some embodiments, the method further comprises subjecting the implant to surface preparation techniques to form the adherent oxide.

In some embodiments, the method comprises the steps of: oxidizing a Zirconium-2.5 wt % niobium alloy sample in a convection furnace in air (about 760 Torr) at 635° C. for 110 minutes placing the sample in a vacuum furnace and controlling the partial pressure of nitrogen, pumping the pressure of the furnace under 10-4 Torr, heating the samples to 685° C. in approximately 1 hour, introducing high purity nitrogen gas and maintaining the partial pressure between 400 to 500 mTorr, maintaining the samples under an atmosphere of nitrogen at a temperature of 685° C. for 7.5 hours, cooling the samples to room temperature under nitrogen atmosphere in 30 minutes; and, sectioning the samples and evaluating the samples using metallographic techniques.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
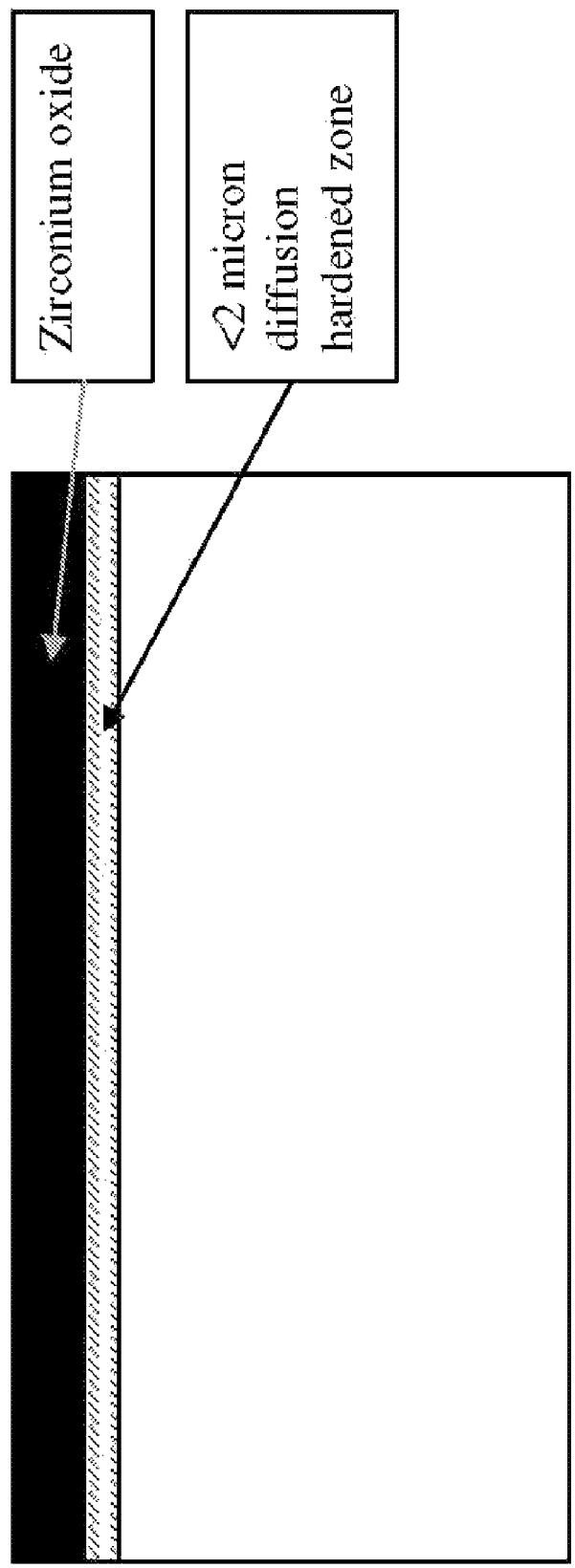
FIG. 1 shows a cross-section of a Davidson-type oxidized zirconium material.
Figure 2:
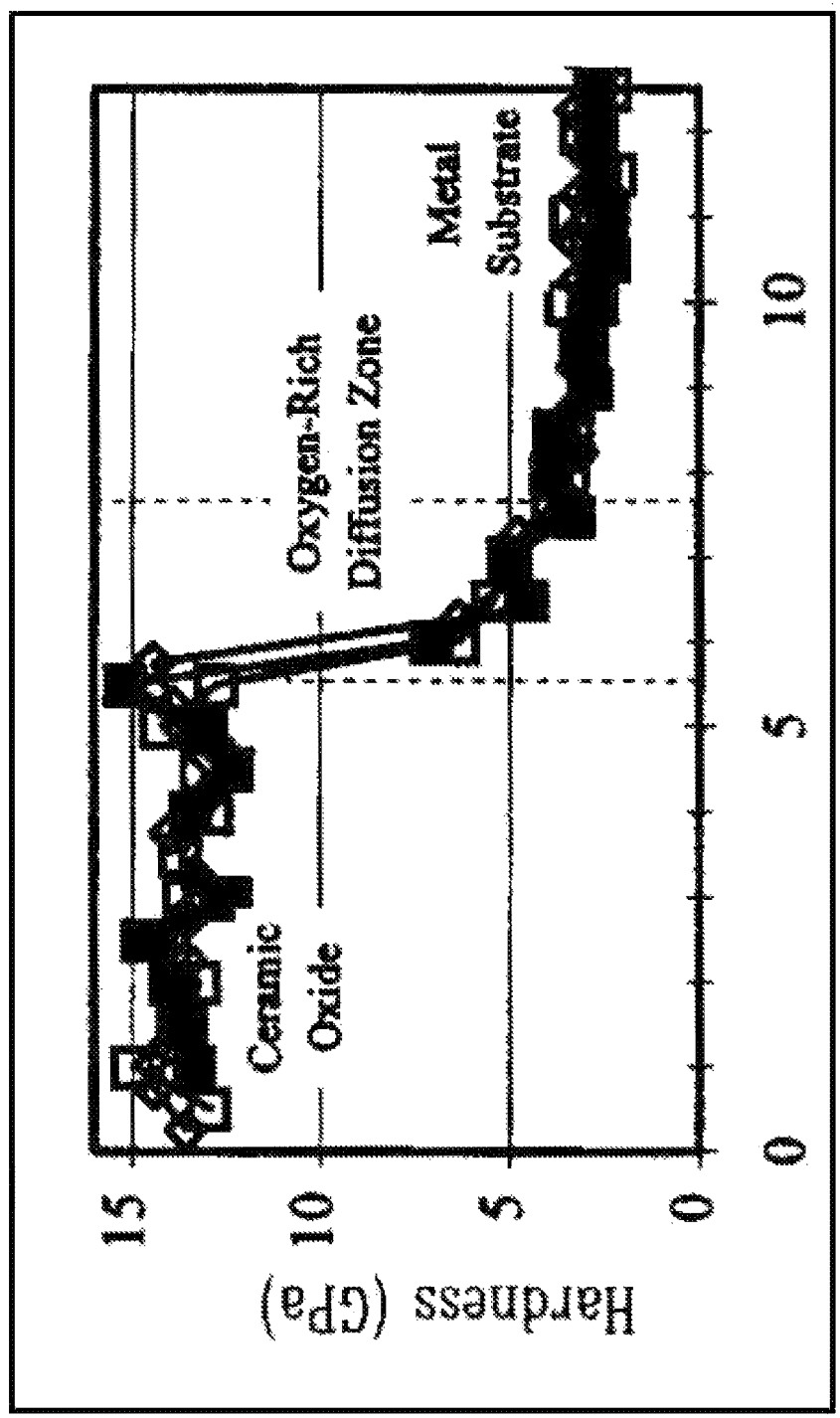
FIG. 2 shows a hardness profile of the Davidson-type oxidized zirconium of FIG. 1.

As used herein, "a" or "an" means one or more. Unless otherwise indicated, the singular contains the plural and the plural contains the singular. For example, when referring to "a" layer, it should be understood to mean "one or more" layers, unless it is otherwise indicated or clear from the context that reference is being made to a single layer.

As used herein, "zirconium alloy" is defined broadly, and includes alloys having at least 5% (w/w) zirconium. In addition to zirconium, the alloys may comprise one or more of titanium, hafnium and niobium. The alloys can be polycrystalline or amorphous or single crystals or combinations of same.

As used herein, "ceramic" is defined as a chemical compound of a metal (or a metal constituent in an alloy) and one or more non-metals, including carbon, oxygen, nitrogen, boron, and combinations thereof. As used herein, "ceramic layer" is defined as a stratum of material consisting of ceramic which forms a part of a greater material. As used herein, the term "ceramic coating" refers to a surface transformed layer, surface film, surface oxide, nitride, carbide, boride (or combination thereof) present on the alloy or metal substrate.

As used herein, "ceramic-forming species" is defined as oxygen, carbon, nitrogen, boron, and any combination thereof. It is preferable that the ceramic-forming species be in the gas phase during the formation of the ceramic layer, although it is possible and within the scope of the present invention wherein the ceramic-forming species is present in a phase other than the gas phase. One non-limiting example of a non-gas phase embodiment is wherein the ceramic-forming species is in the solid phase in contact with the substrate to which it is to be introduced. The ceramic-forming species, in addition to forming a ceramic, also acts as a diffusion hardening species in the formation of a diffusion zone.

The "diffusion zone" is defined as the zone below the ceramic surface and that comprises a diffusion hardening species. "Diffusion hardening species" is defined as carbon, oxygen, nitrogen, boron, or any combination thereof. The "diffusion hardened zone" is defined as that portion of the diffusion zone having hardness at least 1.1 times greater than the substrate hardness.

As used herein, "biocompatible alloy" is defined as the alloy combinations that are currently used in orthopedic industry. Examples of such alloys include cobalt-chromium-molybdenum, titanium-aluminum-vanadium, nickel-titanium and zirconium-niobium. The other biocompatible alloys that are referred to are the alloys that are made from either zirconium or titanium or tantalum or niobium or hafnium or combination thereof.

As used herein, the term "vacuum" refers to a pressure of less than about $10^{-2}$ Torr. The reactive gas is a gas which reacts with the material to either saturate the material or form a ceramic layer. Non-limiting examples of reactive gases include nitrogen, methane, ammonia, nitrous oxide, acetylene, butane, etc. The inert gas is the gas which does not react with the material. Examples of inert gases include helium, neon, argon and krypton.

Figure 3:
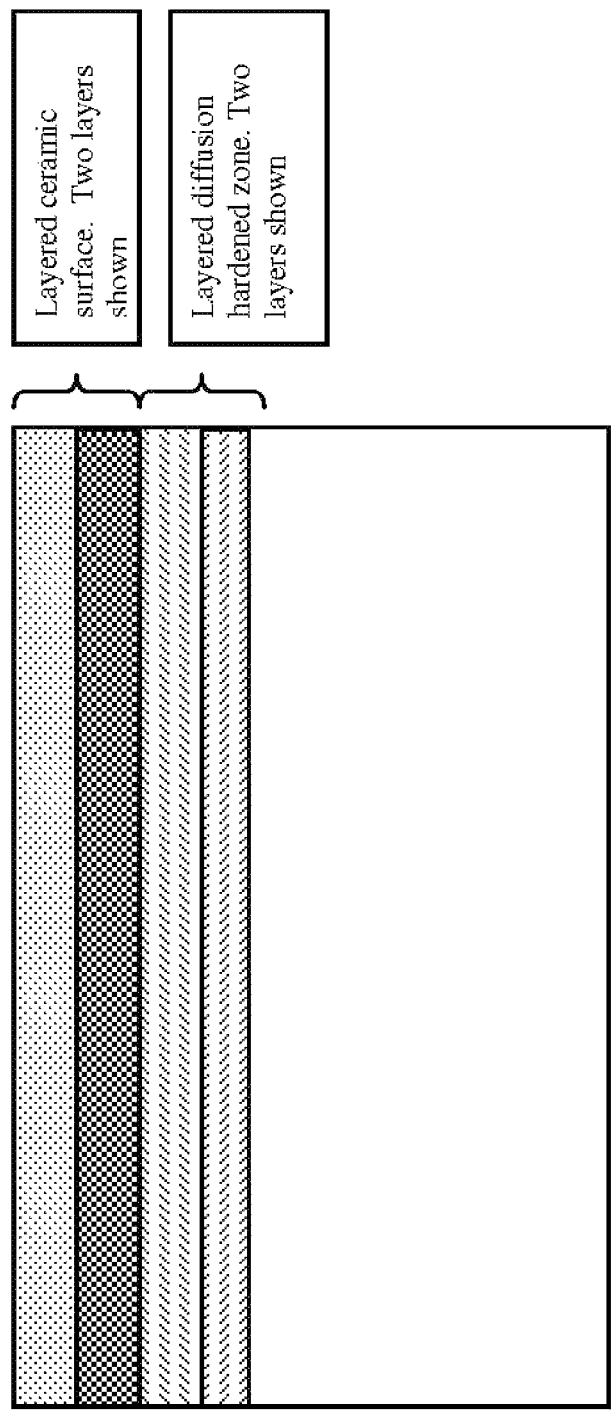
FIG. 3 shows a schematic of a cross-section of a layered structure having a ceramic surface and diffusion zone.

In one aspect of the present invention, there is a medical implant comprising: a substrate comprising zirconium or zirconium alloy; a diffusion hardened zone in contact with the substrate, the diffusion hardened zone comprising zirconium or zirconium alloy and a diffusion hardening species, the diffusion hardened zone having a thickness of greater than 2 microns; and, a layered ceramic layer in contact with the diffusion hardened zone. The layered ceramic surface is comprised of at least two layers. An individual ceramic layer comprises zirconium (Zr) and oxygen, nitrogen, boron, or carbon. Typically, the individual ceramic layer is composed of zirconium (Zr) and any combination of oxygen, nitrogen, boron and/or carbon. The diffusion hardened zone also comprises a layered structure having at least two layers. The diffusion zone comprises oxygen, nitrogen, boron or carbon or any combinations thereof. FIG. 3 shows a schematic of a cross-section of a layered structure having a ceramic surface and diffusion zone.

Figure 4:
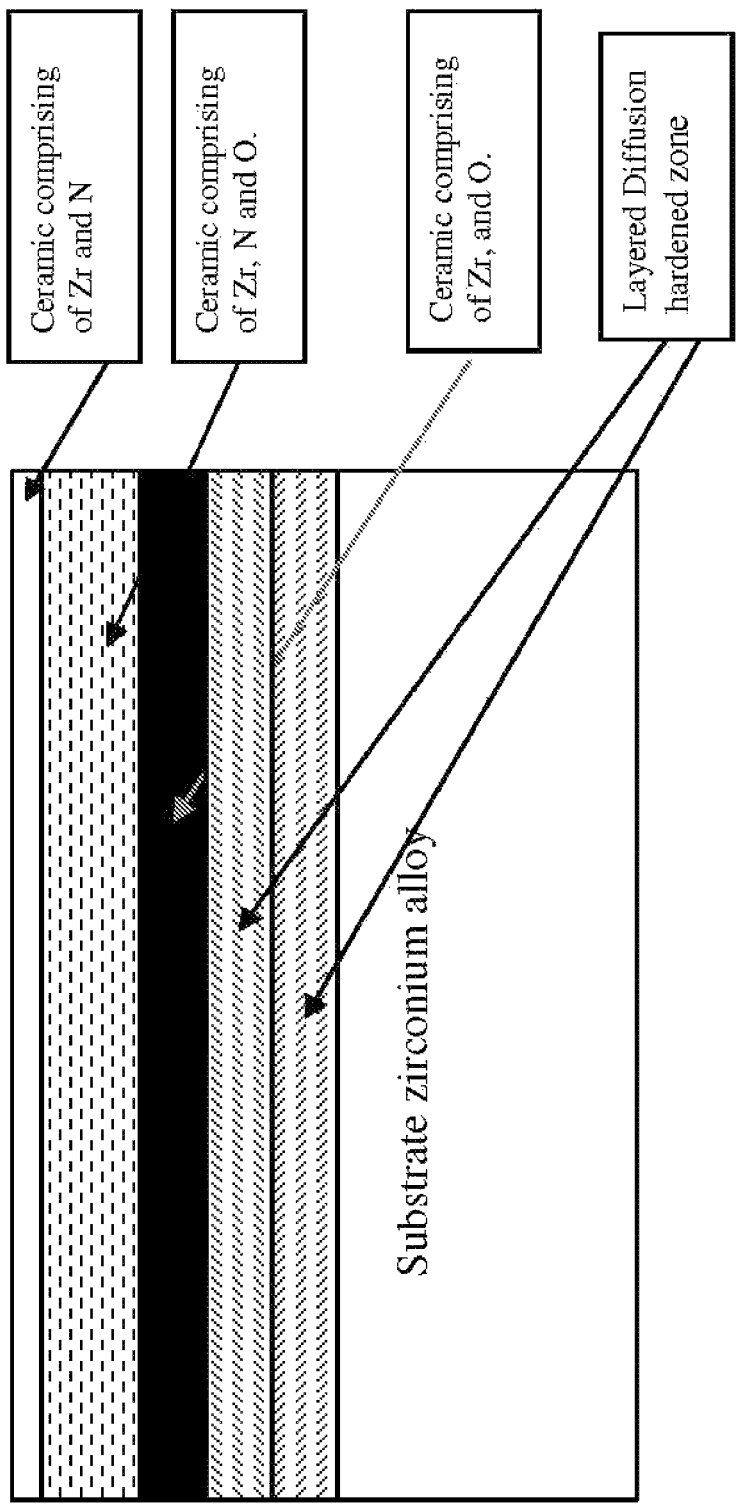
FIG. 4 shows a schematic of a cross-section of a ceramic surface and a diffusion zone wherein the ceramic surface has three layers.

In a specific example, the layered ceramic may consist of three layers, wherein the surface layer of the layered ceramic comprises zirconium, and nitrogen. The second layer adjacent to and directly below the surface layer comprises zirconium, oxygen and nitrogen. The third layer adjacent to the second layer comprises zirconium and oxygen. Below the layered ceramic surface is the layered diffusion zone. The layered diffusion zone is comprised of at least two layers. In both layers, oxygen is the diffusing specie. FIG. 4 shows an example of a substrate (for example of a medical implant) having a three layered ceramic structure and a two layered diffusion zone. The layered structure of the diffusion hardened zone can be detected by metallographic analytical techniques known to those of ordinary skill in the art. These techniques include, but are not limited to, anodization, heat tinting, x-ray diffraction, Auger spectroscopy, depth profiling, etc.

Figure 5:
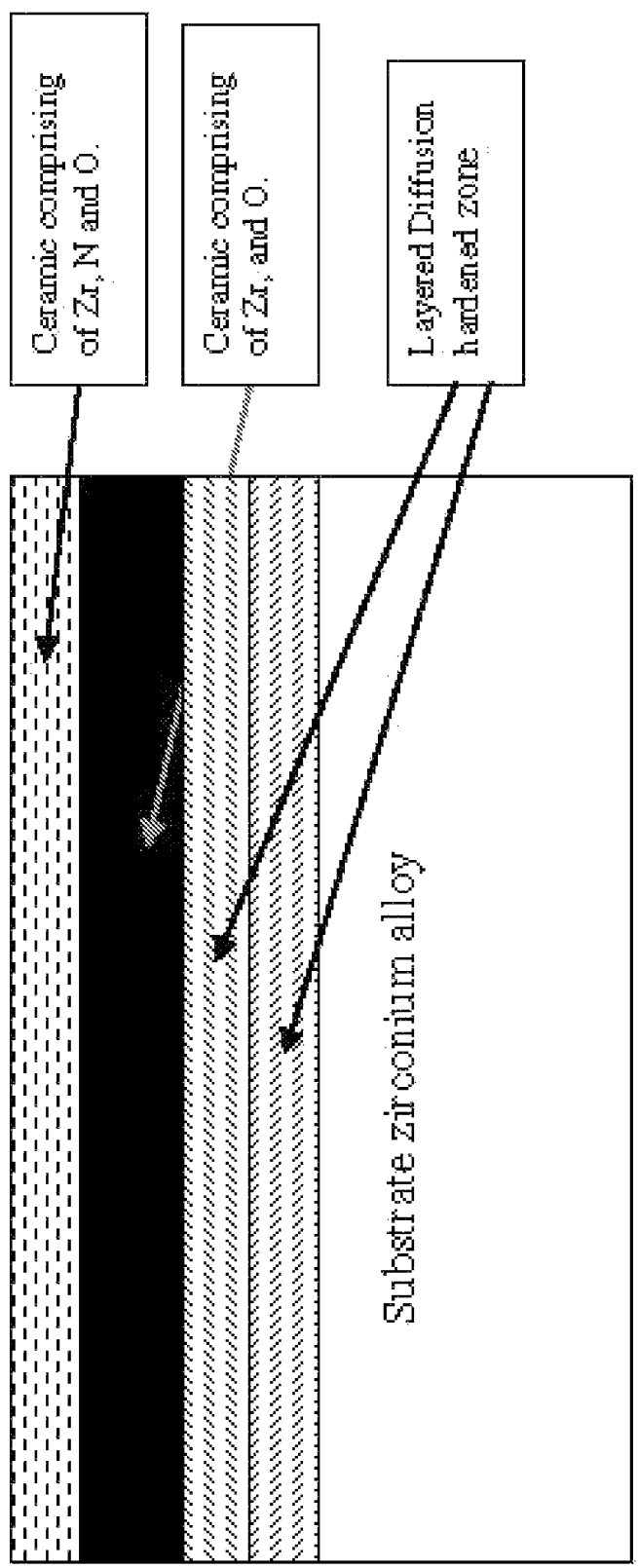
FIG. 5 shows an exemplary schematic of a cross-section of a layered structure having a ceramic surface and diffusion zone wherein the ceramic surface has two layers.
Figure 6:
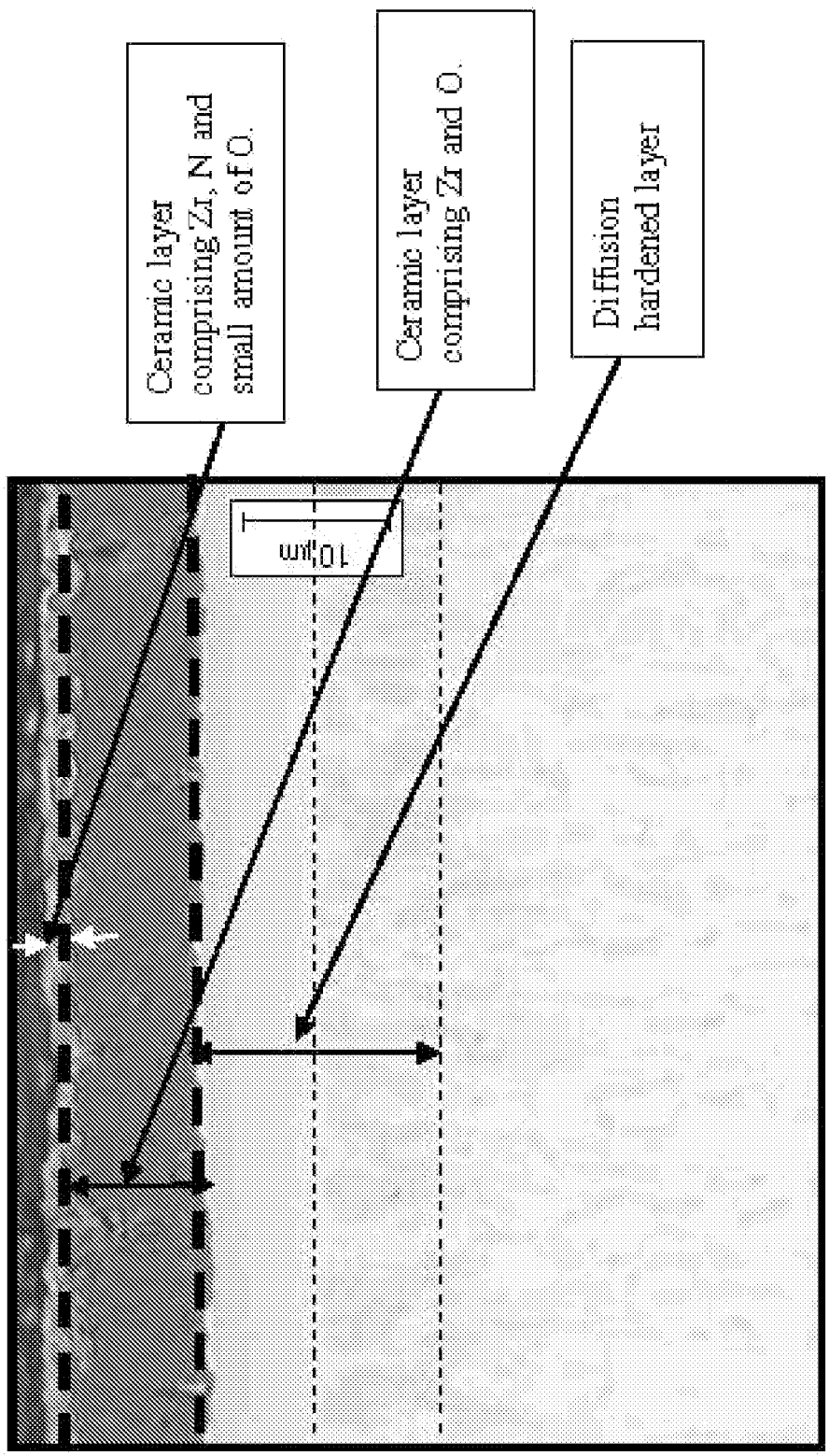
FIG. 6 shows a metallographic cross-section of a layered ceramic structure having a surface and diffusion zone.
Figure 7:
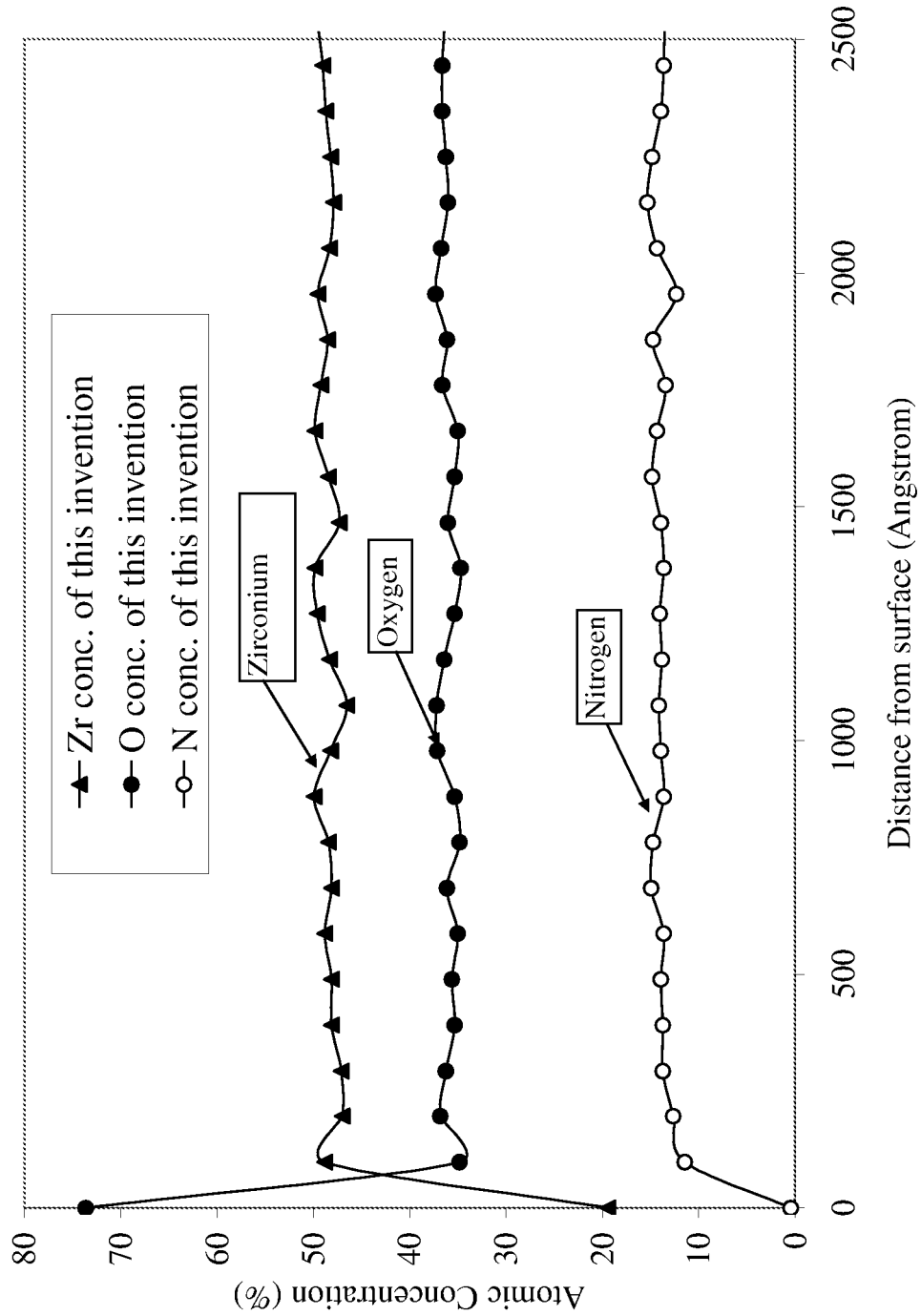
FIG. 7 shows a graph of the atomic concentration of a layered ceramic of the present invention.
Figure 8:
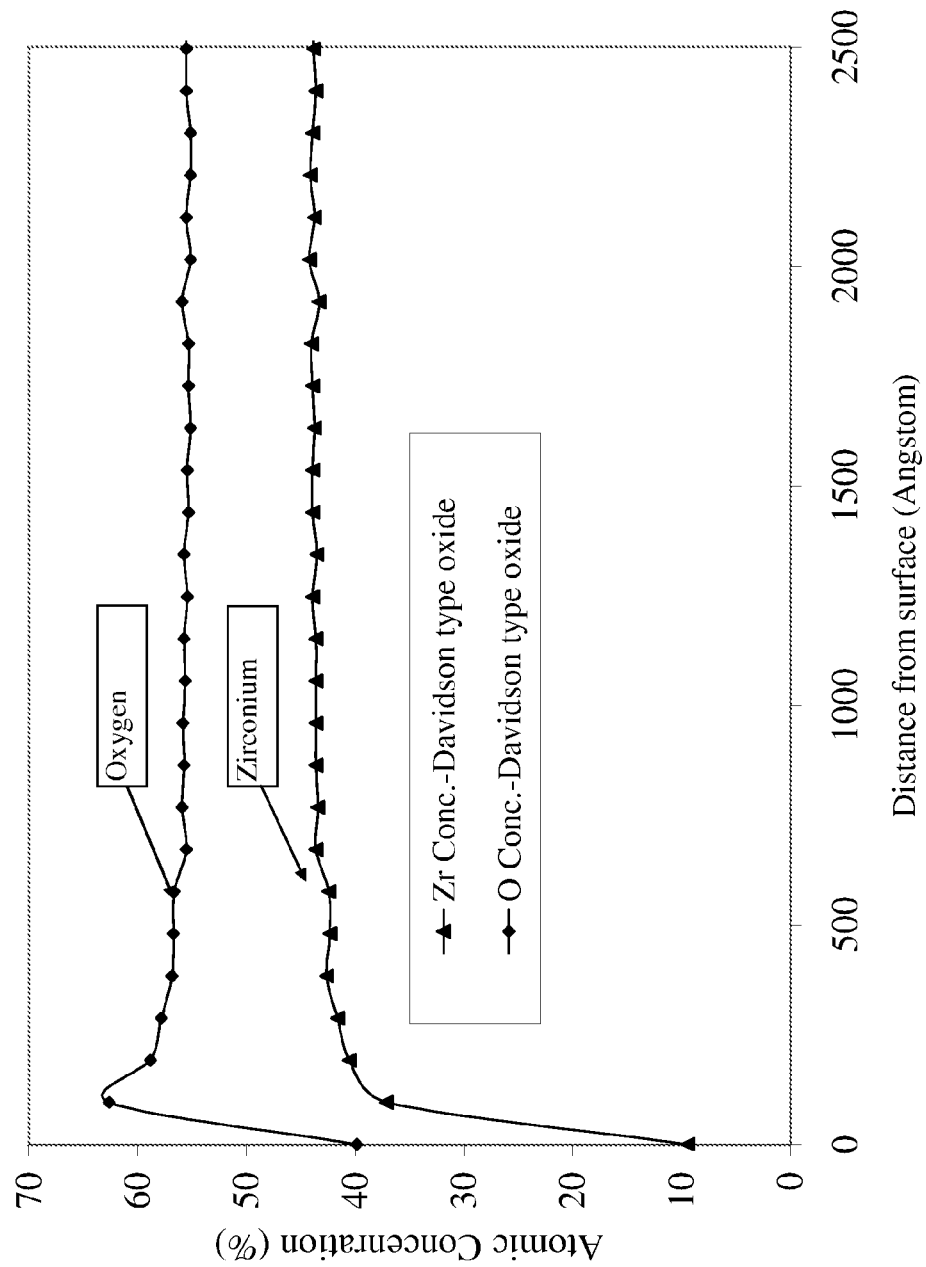
FIG. 8 shows a graph of the atomic concentration of a Davidson-type oxidized zirconium.

In another specific example, the layered ceramic consist of two layers, wherein the surface layer of the layered ceramic comprises zirconium, oxygen and nitrogen. The second layer adjacent to and directly below the surface layer comprises zirconium and oxygen. Below the layered ceramic surface is the layered diffusion zone. The layered diffusion zone comprises at least two layers. In each layer of the layered diffusion zone, oxygen is the diffusing specie. FIG. 5 shows an exemplary layered structure. In some alternate examples, the diffusion hardening specie of the diffusion zone can be oxygen and/or nitrogen. FIG. 6 shows a metallographic cross-section of a ceramic structure having two layers and diffusion hardened zone. FIG. 7 provides compositional data for one of the compositions of the present invention, while FIG. 8 provides analogous data for Davidson-type oxidized zirconium. The Davidson-type oxidized zirconium shows O and Zr whereas, the composition shown in FIG. 7 shows concentrations of Zr, O and N. The analysis shown in FIG. 7 and FIG. 8 was carried out using X-ray photoelectron spectroscopy. The surface was analyzed while being sputtered with an ion gun. It should be noted that the analysis of the top 100 Angstroms is influenced by the contamination of the surface and thus can be ignored.

It should be understood that although examples herein may focus on zirconium alloys, non-alloyed zirconium metal may be used as a substrate within the scope of the present invention.

In yet another example, the layered ceramic consists of two layers, wherein the surface ceramic layer comprises zirconium, oxygen, and nitrogen. The second ceramic layer beneath the top layer comprises predominantly zirconium and oxygen. Below the second ceramic layer is the diffusion hardened zone that consists of two layers. In each layer of the diffusion hardened zone, the diffusion hardening specie is oxygen. The layered structure described above may be produced by following steps:

1. Zirconium-2.5 wt % niobium alloy sample is oxidized in a convection furnace in air at 635° C. for 110 minutes
2. The sample is then put in a vacuum furnace with ability to control the partial pressure of nitrogen.
3. The pressure of the furnace is pumped down below $10^{-4}$ Torr.
4. The samples are then heated to 685° C. in approximately 1 hour.
5. High purity nitrogen gas is then introduced and partial pressure was maintained between 400 to 500 mTorr.
6. The samples are maintained under nitrogen atmosphere at 685° C. for 7.5 hours.
7. The samples are cooled to room temperature under nitrogen atmosphere in 30 minutes.

The samples are then sectioned and evaluated using metallographic techniques known in the art.

The time, temperature, pressure, and gas compositions are varied during the steps described above to produce various embodiments of the present invention. For example, in order to form zirconium carbide on the surface, methane or any other carbonaceous gas can be used. In another example, to form zirconium carbonitride, a combination of methane and nitrogen are used. In specific cases, ammonia gas is used as a source of nitrogen. The thickness of the surface ceramic layer can be manipulated by adjusting the pressure, temperature and time. Usually, a lower temperature, time and pressure may result in lower ceramic layer thickness.

Typically, the first layer of the diffusion hardened metallic zone underneath the layered ceramic structure has a thickness which is greater than or equal to the thickness of said second layer and of any subsequent layers if present. In various examples of the present invention, the diffusion hardened zone has a thickness ranging from 5 to 70 microns. In other examples, the diffusion hardened zone has a thickness ranging from 10 to 50 microns. Yet in additional examples, the diffusion hardened zone has a thickness ranging from 15 to 30 microns. Typically, the hardness of the diffusion hardened zone is at least 10% greater than that of the substrate. The diffusion hardened zone comprises oxygen. However, the diffusion hardened zone may comprise oxygen, nitrogen, carbon, boron or any combination thereof. The diffusion hardened zone has a concentration of oxygen which decreases in the direction of the substrate, said decrease of oxygen concentration being defined by a function selected from the group consisting of an error function, an exponential function, a near uniform distribution function, and any sequential combination thereof.

Figure 11:
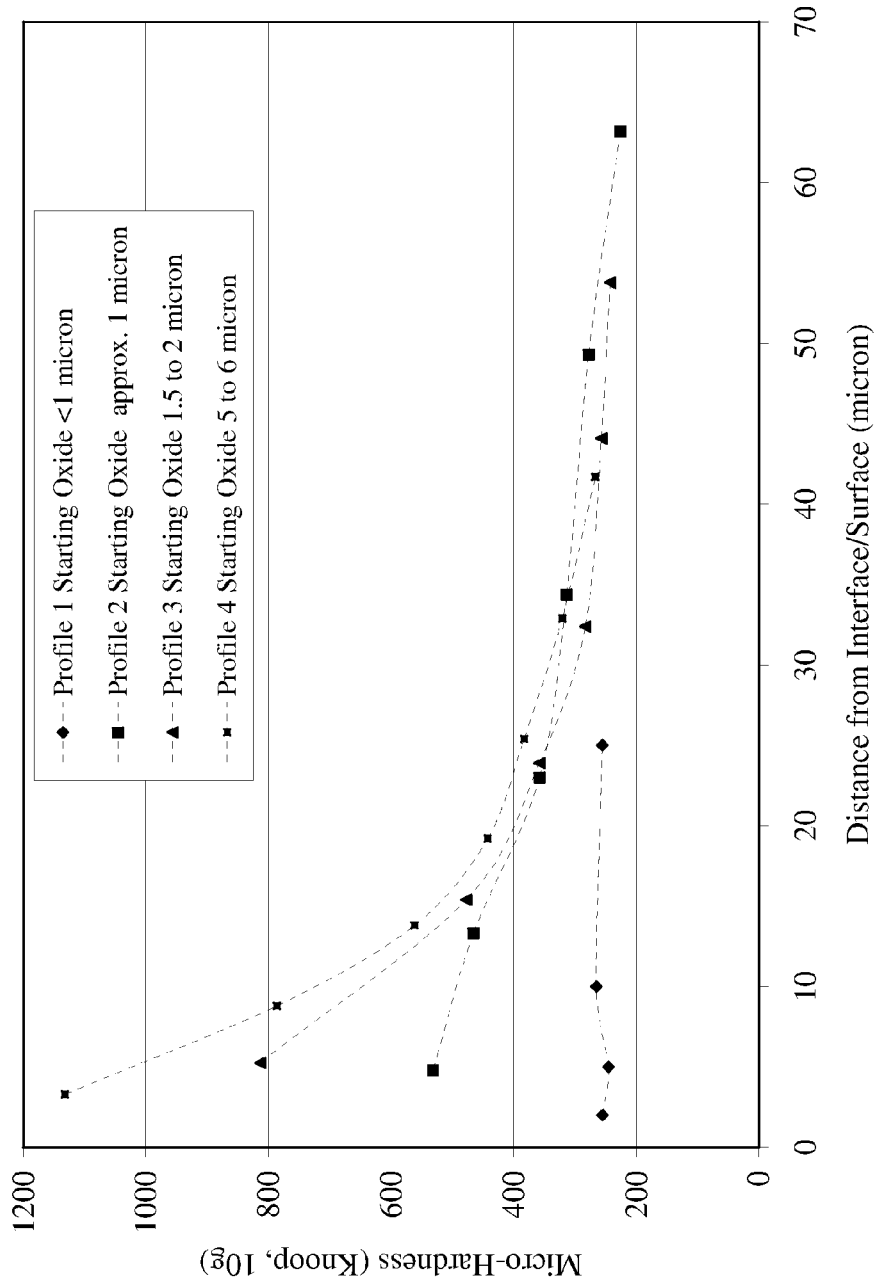
FIG. 11 shows the hardness profiles obtained on Zr-2.5Nb samples after a vacuum diffusion process (685° C. for 10 hrs). The starting oxide represents oxide thickness prior to vacuum diffusion treatment. The oxidation was carried out at 635° C. for different times to produce different starting oxide thickness.

One of the ways to vary the hardness profile of the diffusion hardened zone is to carefully control the oxide thickness before the vacuum diffusion hardening step. FIG. 11 shows four hardness profiles obtained on Zr-2.5Nb alloy samples after vacuum diffusion treatment. The four profiles obtained are Profile 1 (uniform function), Profile 2 (a combination of uniform function and exponential function), Profile 3 (a combination of exponential function and error function), Profile 4 (error-function). The resultant shape of the hardness profile was carefully controlled by the oxide thickness, oxidation and vacuum treatment temperatures and time. In this particular example, the starting oxide thickness was varied by varying oxidation time at a constant temperature of 635° C. Samples were oxidized for 5 minutes, 15 minutes, 30 minutes and 60 minutes respectively. All the samples were vacuum treated at 685° C. for 10 hours. After vacuum treatment the four samples produced four different profiles as shown in FIG. 11. The oxide was retained on sample with profile 4 and the oxide was completely dissolved on samples with Profile 1, Profile 2, and Profile 3. In order to obtain the ceramic layered structure of the samples with Profile 1, the sample is re-oxidized to form at least 1 micron oxide. The oxidation can be done at 600° C. for about an hour. The sample is then placed in the vacuum furnace with ability to control the nitrogen pressure. The sample is heated to 650° C. under vacuum and then the nitrogen gas is introduced and the nitrogen partial pressure of 50 to 500 mTorr is maintained. The process can be run for at least an hour. This will lead to formation of zirconium oxynitride on the surface which is adjacent to zirconium oxide. Zirconium oxide is adjacent to the diffusion hardened zone that has near uniform profile. Similar treatments are done to obtain samples with Profile 2, Profile 3 and Profile 4. Additionally, since the oxide was retained on the sample with Profile 4, the re-oxidation step can skipped and the sample can be directly treated in the nitrogen atmosphere to form zirconium oxynitride or zirconium nitride.

The medical implant of the present invention may be any medical implant, but preferably is a hip implant, a knee implant, or a spinal implant. In a specific example, the layered ceramic forms the surface of a hip implant and it articulates against a similarly layered ceramic implant. The mating surfaces of such implants can be different ceramic or metallic surfaces. For example, a nitrogen enriched surface may be articulated against a carbon enriched surface. In one example, the layered ceramic structure may be coupled with, and articulate against a metallic implant such as CoCr, Ti-6Al-4V, stainless steels etc. In other examples, the layered ceramic structure may be coupled with, and articulate against a ceramic component such as alumina, zirconia, zirconia toughened alumina, silicon nitride etc. Additionally, the layered ceramic implant may be articulated against polymeric components such as made from ultrahigh molecular polyethylene or cross-linked polyethylene. As an alternate illustrative example, the layered ceramic implant is articulated against a hardened CoCr or hardened Ti-6Al-4V implant. The hardening of the CoCr and Ti-6Al-4V implants can be achieved with the techniques known in the art, examples of which include and are not limited to carburization, nitridation and boridation or any combinations thereof. As stated before, other implants that can be used with the present invention include but are not limited to, knee implants, shoulder implants, hip implants, and verterbral implants, for example.

Figure 9:
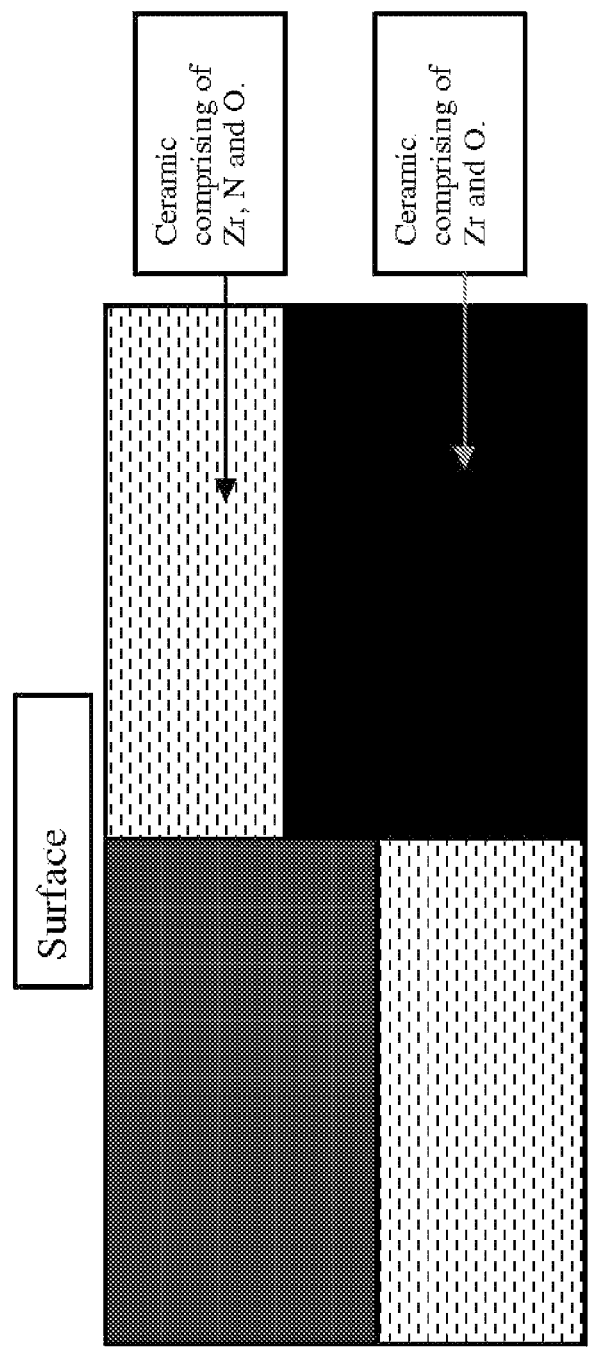
FIG. 9 shows an exemplary schematic of the surface of a patterned ceramic structure.
Figure 10:
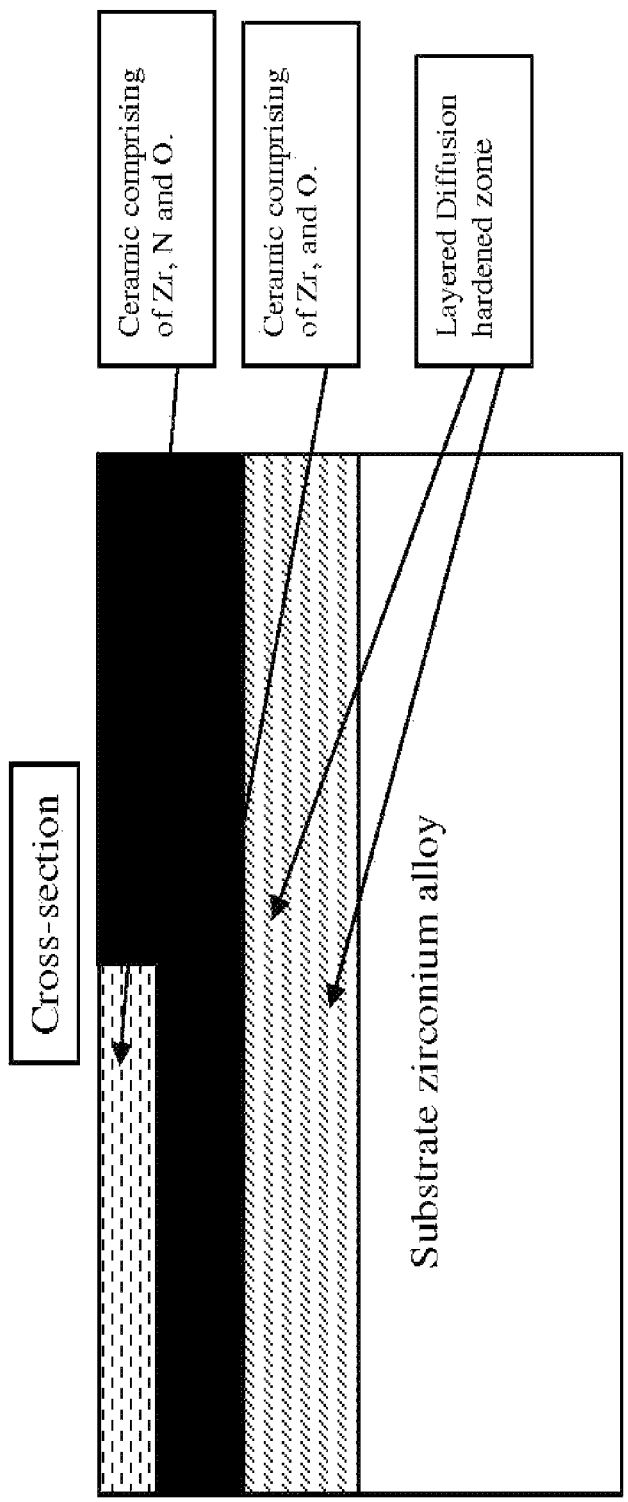
FIG. 10 shows an exemplary schematic of a cross-section of a patterned ceramic structure.

In yet another aspect of the present invention, the layered ceramic surface is patterned. The patterning is achieved in such a way that at least two types of ceramics are exposed on the surface. FIG. 9 shows an example of such structure. The surface is characterized by two different types of ceramic surfaces. FIG. 9 shows only two such areas, but it is easy to conceive that a number of such areas can be made in regular or randomly oriented fashion. FIG. 10 shows a cross-section of the structure shown in FIG. 9. This patterned surface can be made by selectively exposing the oxidized surface to a reactive gaseous specie. For example, the oxidized zirconium surface is patterned with a coating that can withstand the diffusion hardening temperature and process. The patterning of the surface can be achieved by known techniques in the art. The typical steps are applying a photo-resist material on the surface. The material is then selectively cross-linked or hardened using radiation such as ultra-violet light and a mask. After hardening using radiation, the areas that are not cross-linked or hardened are dissolved using organic solvent. Which gives a pattern that will allow only selected areas to be exposed to the nitrogen gas. This process results in nitride formation only in those areas as described in FIG. 9. The cross-linked photo-resist coating is then removed either by chemical or mechanical means giving the structure shown in FIG. 9 and FIG. 10. Once the patterned surface is produced, the pattered surface is articulated against metallic or ceramic implants previously described. In addition to metallic or ceramic implants, the patterned layered structure may be articulated against similarly pattered layered structures.

Typically, thickness of individual ceramic layers range from 0.1 to 10 microns with total thickness of ceramic layers ranging from 0.5 microns to 50 microns. These ranges are not limiting, there are examples wherein the thickness of the ceramic layer and/or ceramic layers are outside of this range. In some cases, the total thickness of diffusion hardened zone ranges from 2 microns to 100 microns.

In the medical implant of the present invention, the ceramic layer may be doped with an element different from which it is made. For example, in such a structure, the zirconium oxide is doped with nitrogen or carbon or boron or any combination thereof. This can be achieved using known techniques in the art. One way to achieve this is to use a nitrogen ion gun. The oxidized sample is put in a vacuum chamber and then high energy nitrogen ions are bombarded on the surface of the oxide. Thus, the nitrogen ions are incorporated in the zirconium oxide surface. A post heating step in vacuum may also be employed which allows the nitrogen ions in the oxide to rearrange.

A typical method of making a layered ceramic medical implant comprises the steps of: (a) forming the medical implant of zirconium or zirconium alloy; (b) treating the implant in the presence of ceramic-forming species at temperature of 500 to 1000° C. for greater than 2 minutes; and, (c) thereafter treating the implant under vacuum or inert gas or a reactive gas such as nitrogen and or methane at a temperature of 500° C. to 1000° C. Variations are possible, for example, in some cases, the step (c) is performed at a temperature of 600° C. to 700° C. In some examples, the steps (a) (b) and (c) are repeated multiple times. This method may be varied in a number of ways. For example, the step (b) is performed for between 5 minutes to 12 hours, the step (c) is performed between 15 minutes to 30 hours, the step (a) is carried out in air, the step (a) is carried out in pure nitrogen, the step (a) is carried out in a methane gas, and/or the step (a) is carried out by putting the specimens in a solid reactive mixture that delivers the ceramic forming specie, for example charcoal powder. Additional examples of varying the typical method of making a layered ceramic medical implant include: the step (b) is carried out in nitrogen atmosphere, the step (b) is carried out in presence of nitrogen and argon gas mixture, the step (b) is carried out in a mixture of methane and nitrogen, the step (b) is carried in a mixture of reactive and inert gases such as argon and nitrogen, and/or where the partial pressure of reactive gases in step (a) and or (b) ranges from $10^{-4}$ to 760 Torr with preferred range for step (b) 0.05 to 500 Torr. In certain aspects of the present invention, the step of forming a medical implant of zirconium or zirconium alloy comprises forming the medical implant of zirconium alloy having an alloying element selected from the group consisting of titanium, tantalum, hafnium, niobium, and any combination thereof. In specific examples, the step of forming the medical implant of an alloy made of zirconium and niobium, wherein the alloy has a niobium content of at least 1% (w/w). In additional examples, the step of forming the medical implant of an alloy made of zirconium and niobium, wherein the alloy has a niobium content of at least 10% (w/w). Typically, the step of treating the implant in the presence of ceramic-forming species and the step of thereafter treating the implant under vacuum or inert gas comprise treating the implant with a diffusion hardening species selected from the group consisting of oxygen, nitrogen, boron, carbon, and any combination thereof.

The appearance of the surface of the medial implants of the present invention ranges from bronze to golden yellow based on the layered structure and thus completely distinguishes itself from the bluish-black surfaces of Davidson-type surfaces. In one such composition the implant is layered with zirconium nitride on the surface. This nitrogen enriched surface is harder than the oxide. Below this nitrogen enriched layered ceramic surface is bluish-black zirconium oxide and below this oxide is a thicker diffusion hardened zone than that obtained by Davidson-type surfaces. This unique structure also overcomes adhesion issues of zirconium nitride to the zirconium alloy substrate. The zirconium nitride surface is adhered to the zirconium oxide which in-turn is very well adhered to the zirconium alloy substrate.

It is important to note that the surface ceramic layer may be completely or partially removed during subsequent manufacturing steps.

The resulting surface composition can be subject to a variety of surface preparation techniques after the step of diffusion-hardening to form the adherent oxide. Such techniques include, but are not limited to, those techniques known in the art to be applicable to diffusion-hardened surfaces. It is expected that other, more rigorous techniques are applicable to the composition due to its greater degree of damage resistance.

The new composition has application in medical implants of all varieties. It is expected to be particularly beneficial for use in articulating implants, such as, but not limited to hip and knee implants. The medical implant of the present invention may be used in other biomedical applications such as spinal devices, small joints, shoulder joints, etc.

The composition of the present invention is applicable for any and all medical implants, but in particular for articulating medical implants such as, but not limited to, hip, knee, shoulder, elbow orthopedic implants, etc. Vertebral implants are also amenable to the compositions described above. The present compositions also find applicability to any and all non-articulating medical implants. The improved characteristics of these implants is seen in comparison to the oxides of the Davidson-type, such as those described in U.S. Pat. No. 5,037,438 to Davidson and U.S. Pat. Nos. 6,447,550; 6,585,772 and U.S. Patent Publication No. 2006/0058888 to Hunter and to described by Pawar et al. in U.S. Patent Publication No. 20070137734.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical implant comprising:
a substrate comprising zirconium or zirconium alloy; a diffusion hardened zone in contact with said substrate, said diffusion hardened zone comprising zirconium or zirconium alloy and a diffusion hardening species, said diffusion hardened zone having a thickness of greater than 2 microns; and a ceramic zone having a layered structure comprising three layers and having:
a surface layer comprising zirconium and nitrogen, a second layer adjacent the surface layer comprising zirconium, oxygen and nitrogen, and a third layer adjacent to the said second layer comprising zirconium and oxygen, wherein said ceramic zone is in contact with said diffusion hardened zone, and said ceramic layers range in thickness from 0.1 to 25 microns; and wherein the total thickness of the ceramic zone and the diffusion hardened zone is 5 microns or greater.

2. The medical implant of claim 1, wherein a layer in the ceramic zone comprises zirconium, oxygen, nitrogen, boron, carbon or any combination thereof.

3. The medical implant of claim 2, wherein the substrate further comprises titanium, tantalum, hafnium, niobium, or any combination thereof.

4. The medical implant of claim 2, wherein individual layers of the layered ceramic zone have a thickness of 0.1 micron to 10 microns.

5. The medical implant of claim 2, wherein the total thickness of the layered ceramic zone is 0.5 micron to 50 microns.

6. The medical implant of claim 1, wherein the ceramic zone forms a surface of said implant and said layered diffusion zone lies below said ceramic zone.

7. The medical implant of claim 1, wherein the diffusion hardened zone has a layered structure comprising at least two distinct layers under metallographic analysis.

8. The medical implant of claim 7, wherein said diffusion hardened zone comprises a diffusion hardening species selected from the group consisting of oxygen, nitrogen, boron, carbon, and any combination thereof.

9. The medical implant of claim 8, wherein said diffusion hardening species comprises oxygen, and/or nitrogen.

10. The medical implant of claim 8, wherein the diffusion hardened zone has a concentration of oxygen which decreases in the direction of the substrate, said decrease of oxygen concentration being defined by a function of selected from the group consisting of an error function, an exponential function, near uniform distribution function, and any sequential combination thereof.

11. The medical implant of claim 7, wherein said first layer of said diffusion hardened zone has a thickness which is greater than or equal to the thickness of said second layer and of any additional layers if any said additional layers are present.

12. The medical implant of claim 7, wherein said diffusion hardened zone has a thickness of 5 to 70 microns.

13. The medical implant of claim 7, wherein said diffusion hardened zone has a thickness of 10 to 50 microns.

14. The medical implant of claim 7, wherein said diffusion hardened zone has a thickness of 2 microns to 100 microns.

15. The medical implant of claim 7, wherein the hardness of the diffusion hardened zone is at least 10% greater than that of the substrate.

16. The medical implant of claim 1, wherein said substrate comprises an alloy of zirconium and niobium and has a niobium content of at least 1% (w/w).

17. The medical implant of claim 1, wherein said substrate comprises an alloy of zirconium and niobium and has a niobium content of at least 10% (w/w).

18. The medical implant of claim 1, wherein said medical implant is selected from the group consisting of a shoulder implant, elbow orthopedic implant, vertebral implant, a hip implant, a knee implant, and a spinal implant.

* * * * *